United States Patent [19]

Minerd et al.

[11] Patent Number: 4,540,887
[45] Date of Patent: Sep. 10, 1985

[54] HIGH CONTRAST RATIO PAPER SENSOR

[75] Inventors: Timothy M. Minerd, Pittsford; Robert E. Crumrine, East Rochester, both of N.Y.

[73] Assignee: Xerox Corporation, Stamford, Conn.

[21] Appl. No.: 461,907

[22] Filed: Jan. 28, 1983

[51] Int. Cl.³ .............................................. G01N 21/86
[52] U.S. Cl. .................................. 250/561; 250/223 R
[58] Field of Search ................. 250/221, 222.1, 223 R, 250/571, 572, 559, 562, 563, 561; 356/446, 448, 443–445; 271/258, 259, 262, 263

[56] References Cited

U.S. PATENT DOCUMENTS

| 3,435,240 | 3/1969 | Brunton | 250/219 |
| 3,827,808 | 8/1974 | Cho | 250/571 |
| 3,882,308 | 5/1975 | Daughton et al. | 356/435 |
| 4,092,068 | 5/1978 | Lucas et al. | 356/73 |
| 4,217,491 | 8/1980 | Dufford et al. | 250/223 R |
| 4,352,988 | 10/1982 | Ishida | 356/435 |

Primary Examiner—David C. Nelms
Attorney, Agent, or Firm—Ronald F. Chapuran

[57] ABSTRACT

A high contrast ratio sensor is provided by introducing a pair of photodetectors into the sensor circuitry. One of the detectors is a diffuse detector and the other is either a reflective or transmittance detector. The two photodetectors are connected in a manner to cause the diffuse detector output to subtract from the reflective (or transmissive) detector output. This subtraction of signals provides a high contrast ratio. In a first embodiment, a diffuse detector and a reflectance detector are located on the same side of the paper as the emitter light and in a second embodiment a diffuse detector and a transmittance detector are located on opposite sides of the paper to be sensed.

6 Claims, 6 Drawing Figures

HIGH CONTRAST RATIO PAPER SENSOR

This invention relates to paper sensors and in particular to a high contrast ratio paper sensor for use in a reproduction machine.

Typical prior art sensors are shown in U.S. Pat. Nos. 3,435,240 and 4,092,068. In U.S. Pat. No. 3,435,240, the surface characteristics of a material are determined by the quotient of output signals from two photomultipliers. The magnitude of these signals from the photomultipliers is determined by the simultaneous transmittance of energy from a single light source through small and large areas of a material being examined. In U.S. Pat. No. 4,092,068, a single light source is directed onto a material surface and the surface characteristics are examined by comparing the amount of light reflected at two different angles from the surface onto a pair of detectors.

It is also known in the prior art to provide sensors to be able to detect translucent papers. One technique comprises a light emitter on one side of the paper path and a transmittance detector on the other side of the path. As paper enters the path between the emitter and detector, the light may be attenuated sufficiently through the paper in order that the signal sensed by the detector indicates paper in the path. The difficulty is that the sensor circuitry is generally tuned only to detect paper having a particular transmittance characteristic. For papers or documents having different transmittance characteristics, the sensor circuitry is often insensitive to be able to detect this type of paper without adjustments having to be made to the sensor circuitry.

Another technique of paper sensing is to provide a reflectance detector on the same side of the paper as the light emitter. With paper in the path, a predetermined amount of light will be reflected from the paper to the reflectance detector to indicate the presence of paper. Here again, the sensing circuitry is often sensitive only to a document or paper having certain transmittance characteristics and for papers with different characteristics, it is necessary to adjust the detector circuitry. This is due to the fact that the present sensors systems have a wide range of characteristics and therefore very low effective contrast ratios. Because of the low contrast ratios obtained in a manufacturing or field environment, electrical and/or mechanical adjustments are required for different documents. The need for readjustment for different types of papers often renders the sensors impractical for use in applications having a wide variety of papers.

It would be desirable, therefore, to provide a relatively simple paper sensor detector that provides a relatively high contrast ratio and that can be used in a variety of paper sensing applications without the need for adjustment.

Accordingly, it is an object of the present invention to provide a relatively high contrast ratio paper sensor to be used for detecting papers having various transmittance characteristics and that can be used in a variety of paper sensor applications. Further advantages of the present invention will become apparent as the following description proceeds and the features characterizing the invention will be pointed out in the claims annexed to and forming a part of this specification.

Briefly, a high contrast ratio sensor is provided by introducing a pair of photodetectors into the sensor circuitry. One of the detectors is a diffuse detector and the other is either a reflective or transmittance detector. The two photodetectors are connected in a manner to cause the diffuse detector output to subtract from the reflective (or transmissive) detector output. This subtraction of signals provides a high contrast ratio. In a first embodiment, a diffuse detector and a reflectance detector are located on the same side of the paper as the emitter light and in a second embodiment a diffuse detector and a transmittance detector are located on opposite sides of the paper to be sensed.

For a better understanding of the present invention, reference may be had to the accompanying drawings wherein the same reference numerals have been applied to like parts and wherein.

Figure 1:
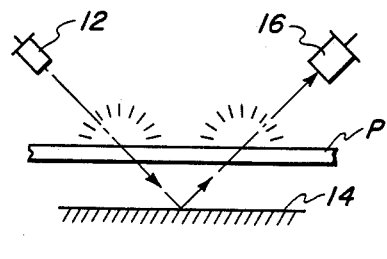
FIG. 1 is a prior art reflectance detector.

With reference to FIG. 1, there is shown a prior art reflectance detector sensor. Without paper in the paper path, a sufficient amount of light emitted from the light source 12 reflects from the mirror 14 to the detector 16 to indicate no paper. With paper 18 in the paper path, it is assumed that the light will be attenuated enough by the paper so that the amount of light reflected from mirror 14 to the reflectance detector 16 has diminished sufficiently to indicate the presence of paper in the path. Unfortunately, with highly translucent paper, not enough light will be attenuated by the paper such that the detector will not recognize the presence of the paper. Some of the light is diffused but some is passed through the paper reflected off the mirror and goes back up through the paper again.

Figure 2:
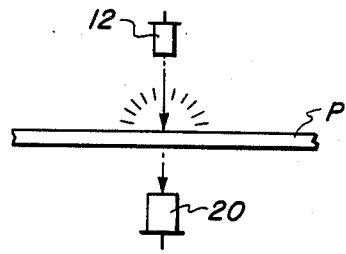
FIG. 2 is a prior art transmittance detector.

FIG. 2 shows another prior art sensor embodiment. In this case, the reflectance detector 16 has been replaced by transmittance detector 20.

Figure 3:
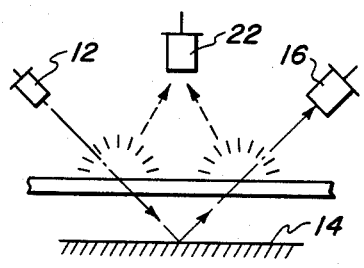
FIG. 3 is a reflectance detector sensor incorporating the present invention.

In accordance with the present invention as seen in FIG. 3, an additional detector, a diffuse detector 22 is inserted into the sensor of FIG. 1. This detector senses light that is diffused by the paper, that is, is not transmitted through the paper. Also, some of the light that is transmitted through the paper and reflected from the mirror 14 is diffused and scattered. Some of this light also is sensed by the diffuse detector 22. It should be noted that the diffuse detector 22 is positioned to minimize detection by detector 22 of light reflected from mirror 14 with no paper present. Thus, if there is a narrow light beam from source 12 so that no light is reflected from mirror 14 to detector 22, then the position of detector 22, as shown, is suitable. This configuration will give a high contrast ratio and a great deal of latitude in selecting components.

If the light from source 12 is not narrow, it may be necessary to move the detector 22 out of the range of the reflected beam. If the detector is not moved, there will be a reduced output signal from sensor. Therefore, there would be a decreased signal to noise ratio and a decreased maximum achievable contrast ratio.

Figure 4:
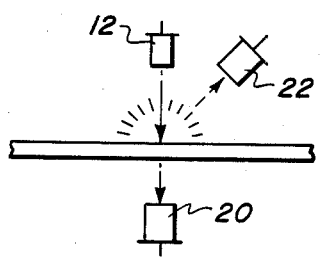
FIG. 4 is a transmittance detector sensor incorporating the present invention.

FIG. 4 is the prior art sensor of FIG. 2 modified in according to the present invention. In particular, a diffuse detector 22 has been added to sense diffused light.

Figure 5:
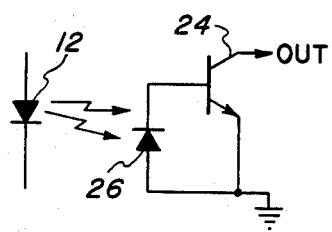
FIG. 5 is an electrical schematic representing the configuration of FIGS. 3 and 4.

FIG. 5 is an electrical schematic representing the detector of FIG. 3. In particular, the light from the suitable light source 12 (any suitable light emitter such as an LED) is received by a transistor 24 representing the reflectance detector 16 and a diode 26 representing the diffuse detector 22. The result is a negative feedback circuit in which one detector is looking for the absence of light while the other is looking for the presence of light. The signal from the diode 26 subtracts from the current through transistor 24 and then from the output of transistor 24.

Figure 6:
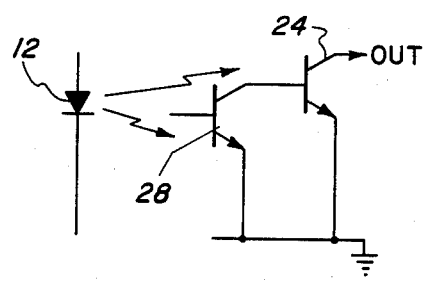
FIG. 6 is an alternative electrical schematic.

In operation, the more reflection of light from the paper, the more light diffusion there will be. The more light diffusion means more light will be subtracted from the amount of light received by the reflectance detector 16. This increases the attenuation of the light sensed by the reflectance detector 16. Also, the more light that is detected by the diffuse detector 22, the more current is subtracted away from transistor 24. The more the current that is subtracted, the less the gain from the transistor 24. As shown in FIG. 6, the diode 26 could be replaced by transistor 28.

In the ideal situation, the output signal from the transistor 24 is 0 when there is paper in the paper path and is at some high level when there is no paper in the paper path. If the diffuse detector 22 is relatively sensitive, it will shut the transistor 24 off and the current will be 0 through the transistor 24.

When a document enters the sensing area, the light reaching the reflective or transmissive detectors 16, 20 is attenuated by the document. This reduces the output current of the transistor 24. However, the diffuse detector 22 now receives light energy and its output current therefore increases. Since the output current from transistor 24 is the difference between its base current due less the output current of diode 26 or transistor 28 the total output current from transistor 24 is greatly reduced. This increases significantly the sensor's contrast ratio.

By proper selection of transistor and diode components, it is possible to achieve a high contrast ratio using the present invention. This can be understood with reference to the following calculations:

$$C.R. = \frac{I_{C24}(NP)}{I_{C24}(P)} \approx \frac{\beta I_{B24}(NP)^*}{\beta I_{B24}(NP)} \quad (1)$$

*Assuming the gain of the 24 is equal for both the paper and no paper conditions.

$I_{C24}$ is the collector current of 24 in the configuration of FIG. 1 or 3.

$$C.R. = \frac{I_{B1}(NP) - I_{26}(NP)}{I_{B1}(P) - I_{26}(P)} \quad (2)$$

Where $I_{B1}$ is the base current of transistor 24 without 26 or 28 connected as in the original sensor arrangement of FIG. 1.

$$\text{If } \frac{I_{B1}(NP)}{I_{B1}(P)} = \frac{10}{1} \text{ and } \frac{I_{26}(P)}{I_{26}(NP)} = \frac{10}{1} \text{ and} \quad (3)$$

$$\frac{I_{B1}(NP)}{I_{26}(P)} = \frac{15}{1}$$

$$\text{Then } C.R. = \frac{I_{B1}(NP) - 1/10 \, I_{26}(P)}{1/10 \, I_{B1}(NP) - I_{26}(P)} =$$

$$\frac{15 \, I_{26}(P) - 1/10 \, I_{26}(P)}{1.5 \, I_{26}(P) - I_{26}(P)} = \frac{14.9}{.5} = 29.8$$

Thus, yielding approximately a 3:1 improvement in C.R.

Thus, if (4)

$$\frac{I_{B1}(NP) = CRO}{I_{B1}(P) = \text{Contrast Ratio of Original Sensor}} \text{ and}$$

$$\frac{I_{26}(P) = CRA}{I_{26}(NP) = \text{Contrast Ratio of Added Sensor}} \text{ and}$$

$$\frac{I_{B1}(NP) = CRX}{I_{26}(NP) = \text{Ratio of Sensor Current With N.P. Condition}}$$

$$\text{Then } CRC = \frac{\frac{I_{B1}(NP) - I_{26}(NP)}{I_{B1}(NP) - CRA \, I_{26}(NP)}}{CRO} =$$

$$\frac{\frac{CRX \, I_{26}(NP) - I_{26}(NP)}{CRX \, I_{26}(NP) - CRA \, I_{26}(NP)}}{CRO}$$

= Contrast ratio of combined sensors.

$$= \frac{\frac{CRX - 1}{CRX - CRA}}{CRO} = \frac{CRO \, (CRX - 1)}{CRX - CRA \cdot CRO} =$$

$$CRO \left[ \frac{CRX - 1}{CRX - CRA \cdot CRO} \right]$$

(5) Therefore, if $1 < CRX \leq CRA \cdot CRO$ the maximum combined contrast ratio is achieved.

In practice, a low performance relfective sensor could have a C.R. as low as 20:1 (CRO) and a low performance diffusive sensor could have a C.R. as low as 10:1 (CRA). Thus, CRX should be chosen such that $1 < CRX \leq 200$. Since it is desirable to have as large an output as possible, CRX should be chosen such that $CRX >> 1$.

(6) A practical range of values for CRX might be: $20 \leq CRX \leq 200$ for a combined sensor with a maximum achievable contrast ratio.

With reference to the calculations, ideally it is desirable to have infinite contrast ratio. In other words, a 0 current when there is paper in the paper path and a very high level of current when there is no paper. The contrast ratio is simply the ratio of the current with no paper over the current with paper. To have a high contrast ratio, it is desirable to have very low current when there is paper in the path.

In the contrast ratio equation (2), the numerator of the equation (1) $I_{24}$ (No Paper) has been expressed as the difference of the base current of the transistor 24 as shown in FIGS. 5 and 6 less the current of the diode 26 or transistor 28 or at the base of transistor 24. The numerator of the equation is the same expression for the current with paper in the paper path.

It is desirable to have as a rule of thumb a contrast ratio of 40. However, assume that the contrast ratio is 4 as shown in equations (3). That is the ratio of $I_{B1}$ with no paper over $I_{B1}$ with paper is 4 to 1 and similarly the ratio of $I_{26}$ paper over $I_{26}$ no paper is 4 to 1.

However, we desire a contrast ratio equal to 40 over 1. Substituting in equation (2) the 4 to 1 contrast ratio we get equation (4). Solving for the ratio $I_{B1}$ over $I_{26}$ with no paper results in a 17.7 to 1 ratio. This determines that the ratio of the base current in transistor 24 to the ratio of the current of diode 26 or transistor 28 with no paper must be 17.7 to 1 to provide a 40 contrast ratio.

In other words, the light that the detector 16 or 20 sees must be 18 times greater than the light detector 26 sees to provide a 40/1 contrast ratio.

While there has been illustrated and described what is at present considered to be a preferred embodiment of the present invention, it will be appreciated that numerous changes and modifications are likely to occur to those skilled in the art, and it is intended in the appended claims to cover all those changes and modifications which fall within the true spirit and scope of the present invention.

What is claimed is:

1. Apparatus for determining the presence of paper in a paper path including:
    a source of light disposed near the paper path for emitting light in the direction of the paper path,
    a reflecting surface,
    a first detector disposed near the paper path for detecting a first quantity of light reflected from the reflecting surface when no paper is in the paper path and for detecting a lesser quantity of light reflected from the reflecting surface when paper is in the paper path, the paper in the paper path diffusing a portion of the light emitted by the light source, the improvement comprising:
    a second detector disposed near the paper path to detect light emitted from the source of light and diffused by paper in the paper path, the second detector being electrically connected to the first detector.

2. The apparatus of claim 1 wherein contrast ratio is defined as the ratio of the output current of the first detector without paper in the paper path to the output current with paper in the paper path and the first detector is a phototransistor, the second detector being electrically connected to the base of the phototransistor whereby there is provided an increase in the contrast ratio of the apparatus with the use of the second detector.

3. The apparatus of claim 2 wherein the second detector is a photodiode, the photodiode diminishing the output current of the phototransistor with paper in the paper path whereby the phototransistor senses the presence of paper in the paper path.

4. Apparatus for determining the presence or absence of paper in a paper path including:
    a light source disposed near the paper path for emitting a given quantity of light,
    a light detector disposed opposite the light source for detecting a first quantity of light emitted from the light source with no paper in the paper path and a second quantity of light for detecting when paper is present in the paper path, the paper in the paper path being disposed intermediate the light source and the light detector, a portion of the light emitted from the light source being diffused by the paper in the paper path, and
    a diffuse detector disposed adjacent the paper path for sensing the light that is diffused by the paper in the paper path, the light detector being electrically connected to the diffuse detector.

5. The sensor of claim 4 wherein contrast ratio is defined as the ratio of the output current of the light detector without paper in the paper path to the output current with paper in the paper path and the light detector is a phototransistor, the diffuse detector being electrically connected to the base of the phototransistor whereby there is provided an increase in the contrast ratio of the apparatus with the use of the diffuse detector.

6. The sensor of claim 5 wherein the second detector is a photodiode, the photodiode diminishing the output current of the phototransistor with paper in the paper path whereby the phototransistor senses the presence of paper in the paper path.

* * * * *